(12) United States Patent
Schnyder et al.

(10) Patent No.: US 6,441,233 B1
(45) Date of Patent: Aug. 27, 2002

(54) PROCESS FOR THE PREPARATION OF AROMATIC CARBOXYLIC ACID AMIDES

(75) Inventors: Anita Schnyder, Allschwil; Adriano Indolese, Möhlin, both of (CH); Gerald Mehltretter, Rostock (DE)

(73) Assignee: Solvias AG, Basel (CH)

( * ) Notice: Subject to any disclaimer, the term of this patent is extended or adjusted under 35 U.S.C. 154(b) by 0 days.

(21) Appl. No.: 09/885,103

(22) Filed: Jun. 21, 2001

Related U.S. Application Data

(63) Continuation of application No. PCT/EP99/10127, filed on Dec. 20, 1999.

(30) Foreign Application Priority Data

Dec. 21, 1998 (CH) .............................................. 2523/98

(51) Int. Cl.⁷ ............................................ C07C 231/10
(52) U.S. Cl. ....................... 564/132; 564/169; 564/183; 546/323
(58) Field of Search ................................ 564/132, 169, 564/183; 546/323

(56) References Cited

U.S. PATENT DOCUMENTS 6,326,517 B1 * 12/2001 Kume et al. ................ 564/132

OTHER PUBLICATIONS

Perry, R., et al. "A Novel Palladium–Catalyzed Synthesis of 2–Arylbenzimidazoles", J. Org. Chem., vol. 58 (1993), pp. 7016–7021.

Schoenberg, A., et al. "Palladium–Catalyzed Amidation of Aryl, Heterocyclic, and Vinylic Halides", J. Org. Chem., vol. 39, No. 23 (1974), pp. 3327–3331.

* cited by examiner

*Primary Examiner*—Shailendra Kumar
(74) *Attorney, Agent, or Firm*—Wenderoth, Lind & Ponack, L.L.P.

(57) ABSTRACT

A process for the preparation of primary aromatic carboxamides by the carbonylation of an aromatic compound, which contains at least one leaving group, with carbon monoxide, in the presence of a homogeneous or heterogeneous Pd catalyst and at least stoichiometric amounts of an amidation agent at elevated temperatures, which is characterized in that a primary carboxamide or a primary urethane is used as the amidation agent, and the reaction is carried out in the presence of an acylation catalyst.

21 Claims, No Drawings

PROCESS FOR THE PREPARATION OF AROMATIC CARBOXYLIC ACID AMIDES

This application is a continuation of International Application No. PCT/EP99/10127, filed Dec. 20, 1999, the contents of which are incorporated herein by reference.

BACKGROUND OF THE INVENTION

1. Field of the Invention

The present invention relates to a process for the preparation of primary aromatic carboxamides by reacting aromatic compounds, which contain a leaving group, with carbon monoxide and a primary carboxamide, for example formamide, in the presence of a homogeneous or heterogeneous palladium catalyst and an acylation catalyst at an elevated temperature.

2. Description of the Prior Art

In J. Am. Chem. Soc. 1989, 111, pages 8742 to 8744, Y. Ben-David et al. describe the carbonylation of aryl halides in the presence of a specific Pd(0) phosphine complex, whereby depending on the nucleophile used, for example water, alkanol or secondary amine, arylcarboxylic acids, arylcarboxylates or arylcarboxamides are obtained. If dimethylformamide is used as the solvent during the reaction, it is inert and does not lead to arylcarboxylic acid dimethylamides. Under the conditions of this reaction, the production of primary amides is practically excluded and is also not mentioned.

In Tetrahedron Letters 39 (1998), pages 2835 to 2838, E. Morera et al. describe the preparation of primary aromatic carboxamides, in which an aryl iodide or triflate is carbonylated in the presence of a homogeneous Pd catalyst and hexamethyldisilazane, and afterwards the reaction mixture is worked up hydrolytically. The starting products are expensive and the necessary hydrolytic working up is uneconomical, so that this process is not suitable for use on an industrial scale.

In J. Org. Chem. 1993, 58, pages 7016 to 7021, J. Perry et al. describe the preparation of arylbenzimidazoles by reacting iodine aromatics, 1,2-phenylene and carbon monoxide in the presence of a palladium catalyst and a tertiary nitrogen base in N,N-dimethylacetamide as solvent. It is also mentioned that aromatic N,N-dimethylcarboxamides are produced as a by-product, the formation of which is explained by a decomposition of the solvent.

BRIEF SUMMARY OF THE INVENTION

It has now surprisingly been found that primary aromatic carboxamides are obtained with high selectivity and in a high yield it carbonylation is carried out by starting with aromatic compounds which contain a leaving group, with homogeneous or even heterogeneous Pd catalysts, in the presence of at least stoichiometric amounts of a primary carboxamide, for example formamide, and additionally in the presence of an acylation catalyst. Selectivity and high yields are attained even if N-alkylated carboxamides are used as the solvent.

DETAILED DESCRIPTION OF THE INVENTION

The subject matter of the invention is a process for the preparation of primary aromatic carboxamides by the carbonylation of an aromatic compound, which contains at least one leaving group, with carbon monoxide, in the presence of a homogeneous or heterogeneous Pd catalyst and at least stoichiometric amounts of an amidation agent at elevated temperatures, which is characterised in that a primary carboxamide or urethane is used as the amidation agent, and the reaction is carried out in the presence of an acylation catalyst.

The aromatic compounds in question may be hydrocarbon aromatics or hetero-aromatics. The hydrocarbon aromatics may contain, for example, 6 to 18 carbon atoms, preferably 6 to 14 carbon atoms, most preferably 6 to 10 carbon atoms. The hetero-aromatics may contain, for example 5 to 17 carbon atoms, preferably 5 to 13 carbon atoms, most preferably 4 to 9 carbon atoms, and at least one hetero atom selected from the group O, S, N and P. The aromatic compounds also include aryl- and heteroaryl-vinyls with a leaving group (especially chlorine or bromine) on a vinyl carbon atom.

Examples of hydrocarbon aromatics are benzene, pentalene, indene, indoline, naphthalene, acenaphthylene, anthracene, phenanthrene, fluorene, triphenylene, pyrene, chrysene, naphthacene, biphenyl, biphenylether, 1,4-diphenylbenzene, vinylbenzene and vinyinaphthalene. Benzene, biphenyl and naphthalene are preferred.

Examples of hetero-aromatics are thiophene, vinylthiophene, benzthiophene, furan, benzofuran, pyran, chromene, pyrrole, vinylpyrrole, imidazole, pyrazole, pyridine, vinylpyridine, bipyridyl, pyrazine, pyrimidine, pyridazine, indole, vinylindole, isoindole, 1H-indazole, quinoline, isoquinoline, phthalazine, quinoxaline, quinazoline, carbazole, acridine, phenanthroline, phenazine, thiazole, isothiazole, phenothiazine, oxazole, isooxazole, phenoxazine, pyrazole, piccoline, and lutidine.

The hydrocarbon aromatics and hetero-aromatics may be unsubstituted or substituted by at least one inert substituent, for example 1 to 3 inert substituents. Examples of substituents are $C_1$–$C_8$-, preferably $C_1$–$C_4$-alkyl, $C_1$–$C_8$-, preferably $C_1$–$C_4$-alkoxy, $C_1$–$C_8$-, preferably $C_1$–$C_4$-halogenalkyl, $C_1$–$C_8$-, preferably $C_1$–$C_4$-hydroxyalkyl, $C_1$–$C_8$-, preferably $C_1$–$C_4$-cyanoalkyl, and —CN.

Examples of alkyl substituents are methyl, ethyl, n- and isopropyl, n-, iso- and tert.-butyl, pentyl, hexyl and octyl. Examples of alkoxy substituents are methoxy, ethoxy, n- and isopropoxy, n-, iso- and tert.-butoxy, pentoxy, hexoxy and octoxy. Examples of halogenalkyl substituents are fluoromethyl, difluoromethyl, trifluoromethyl, chloromethyl, dichloromethyl, trichloromethyl, perfluoroethyl, chloroethyl, n- and iso-chloro- or -fluoropropyl, n-, iso- and tert-chlorobutyl. Examples of hydroxyalkyl substituents are hydroxymethyl, β-hydroxyethyl, n-hydroxypropyl and n-hydroxybutyl. Examples of cyanoalkyl substituents are cyanomethyl, 2-cyanoeth-1-yl and 3-cyanoprop-1-yl.

Leaving groups are known and are described in literature. Examples of leaving groups are, in particular, halides such as chloride, bromide and iodide, as well as the group R—S($O_2$)—O—, wherein R is fluorine, chlorine, halogenmethyl, phenyl, halogen-phenyl, mono-, di- or trimethylphenyl or mono-, di- or tri(halogenmethyl)phenyl. Examples are fluorosulphonyloxy, chlorosulphonyloxy, methylsulphonyloxy, trifluoromethylsulphonyloxy, nonaflate and tosylate. Other known leaving groups are aryl-substituted methoxy groups, such as diphenylmethoxy, di(methylphenyl)methoxy, trityl and tri(methylphenyl)methoxy. Preferred leaving groups are halides, especially chloride and bromide.

In the context of the invention, stoichiometric amounts of amidation agent signifies at least an equimolar amount of amidation agent, based on the aromatic compound containing leaving groups, so that there is at least one equivalent of amidation agent per leaving group. The aromatic compound preferably contains two and most preferably one leaving group, so that in this case at least two, or at least one mol of amidation agent is used per mol of aromatic compound. It may be advantageous to use a surplus of amidation agent, for example up to a molar excess of more. A high excess may be used, especially if the amidation agent serves as the solvent at the same time, for example formamide.

The presence of carbon monoxide can mean that the reaction is carried out with pure carbon monoxide, or with mixtures of carbon monoxide with an inert gas, for example nitrogen or noble gases (helium, neon, argon).

The reaction may be carried out under slightly reduced pressure, at normal pressure or preferably at high pressure. High pressure may mean, for example, up to 100 bar, preferably up to 50 bar. The reaction is most preferably carried out at a pressure of 1 to 20 bar, particularly preferably at a pressure of 1 to 10 bar.

Elevated temperature in the context of the invention can mean a temperature range of 30 to 250° C., preferably 50 to 200° C., most preferably 80 to 140° C.

Pd catalysts are known and have been described in literature many times, see for example J. Tsui in Palladium Reagants and Catalysts, John Wiley and Sons (1995). These are generally Pd(0) complexes with ligands from the group mono- and bidentate, tertiary or ditertiary amines, phosphines and arsines. Phosphines are preferred. The N, P and As atoms of the ligands may be substituted by identical or different hydrocarbon radicals having preferably 1 to 18, most preferably 1 to 12, and especially 1 to 8 carbon atoms. The hydrocarbon radicals may be selected from the group linear and branched $C_1$–$C_{12}$-alkyl, cycloalkyl with 5 to 7 ring carbon atoms, which is unsubstituted or substituted by $C_1$–$C_4$-alkyl; $C_6$–$C_{10}$-aryl which is unsubstituted or substituted by $C_1$–$C_4$-alkyl; especially phenyl and alkylphenyls; benzyl which is unsubstituted or substituted by $C_1$–$C_4$-alkyl. Two of the substituents on the N, P and As atoms may also represent an aliphatic hydrocarbon radical which is unsubstituted or substituted by $C_1$–$C_4$-alkyl, and which, together with these hetero atoms, forms a 5- or 6-membered ring; for example two substituents may signify tetramethylene or pentamethylene. With bidentate ligands, two of the N, P and/or As atoms are linked by a linear, bivalent hydrocarbon group, which is unsubstituted or substituted by $C_1$–$C_4$-alkyl, to two to five, preferably two to four carbon atoms, whereby the bivalent hydrocarbon group can be part of a ring or ring system. Suitable bidentate ligands are also those which contain a tertiary amine group and a tertiary phosphine group.

Some examples of ligands are trimethylphosphine, triethylphosphine, tris(t-butyl)phosphine, tricyclohexylphosphine, tri(methylcyclohexyl)phosphine, methyl(tetramethylene)phosphine, t-butyl(pentamethylene) phosphine, triphenylphosphine, tri(methylphenyl) phosphine, 1,2-diphenylphosphine-cyclohexane or -cyclopentane, 2,2'-(diphenylphosphine)biphenyl, 2,2'-(diphenylphosphine)biphenylether, 1,2-bis(diphenylphosphine)ethane, 1,3-bis(diphenylphosphine) propane, 1,4-bis(diphenylphosphine)butane, 3,4-bis(diphenylphosphine)pyrrolidine, 2,2'-(diphenylphosphine)bisnaphthyl (Binap), 1,1'-bis(diphenylphosphin)ferrocene, 1-diphenylphosphine-1'-dicyclohexylphosphine-ferrocen (Josiphos), diphenylphosphine ether (Dpephos), and N-methyl 3,4-diphenylphosphinomethyl-pyrrolidine.

Pd catalysts are generally obtained from Pd(II) or Pd(0) compounds by complexing with ligands. Suitable compounds are, for example, palladium dihalides and diacetate, palladium sulphate, $PdCl_2[P(C_6H_5)_3]_2$, $Pd_2$(dibenzylideneacetone)$_3$ and $Pd[P(C_6H_5)_3]_4$. The catalyst may be produced separately and then used. It is especially advantageous in the process according to the invention to produce the catalyst in situ, whereby a Pd(II) salt which is complexed with ligands is firstly presented or prepared, it required, an excess (for example an equimolar excess) of the ligand is additionally added, the aromatic compound, a formamide, an acylation catalyst and optionally an inert solvent are added. If the reaction is started by applying carbon monoxide and heating the reaction mixture, in the reductive reaction mixture the desired Pd(0) catalyst is formed as a catalytically active element.

As already described, the palladium catalyst can be formed from a heterogeneous catalyst precursor, for example colloidal Pd(0), Pd(0) applied to carrier materials, or Pd(II) compounds applied to carrier materials, for example PdO or Pd(II) salts. Suitable carrier materials are for example inorganic metal oxides, silicates and carbon.

The catalyst may be used in a concentration of 0.001 mol %, to 10 mol %, preferably in a concentration of 0.01 mol % to 5 mol %, most preferably from 0.01 mol % to 3 mol %, based on the aromatic compound.

The carboxamides used according to the invention as amidation agents may be primary carboxamides of mono- or polycarboxylic acids, or urea. They are preferably aliphatic carboxylic acids. The polycarboxylic acids preferably contain 2 to 4, most preferably 2 or 3 carboxyl groups. Suitable carboxamides are at least partially soluble in the reaction medium. The amides may be derived from aliphatic or cycloaliphatic carboxylic acids with for example 1 to 18, preferably 1 to 12 carbon atoms, whereby commercially available, inexpensive carboxylic acids are preferred in particular, since in the process according to the invention the carboxamides serve as amine suppliers for the preparation of other carboxamides. One preferred group is formamide and primary $C_1$–$C_6$-, especially $C_4$–$C_4$-alkylcarboxamides, whereby the alkyl may be linear or branched. Urea and formamide are preferred in particular.

The carboxamides may correspond, for example, preferably to formula I,

$$R_1[C(O)-NH_2]_x \qquad (I),$$

wherein x is 1, and $R_1$ signifies H, $NH_2$, $OR_2$ or linear or branched alkyl with 1 to 6 and preferably 1 to 4 carbon atoms, or wherein x is 2 and $R_1$ signifies a direct bond or linear or branched alkylene with 1 to 6 and preferably 1 to 4 carbon atoms, and $R_2$ is linear or branched alkyl with 1 to 6 and preferably 1 to 4 carbon atoms.

One preferred embodiment of the carboxamides of formula I is the one in which (a) x is equal to 1 and $R_1$ is H, $NH_2$, methyl, ethyl, n- and iso-propyl, n-, iso- and tert.-butyl, and (b) x is equal to 2 and $R_1$ signifies methylene, ethylidene, 2,2-propylidene, ethylene, methylethylene, 1,3-propylene and 1,2-, 1,3- or 1,4-butylidene.

Some preferred examples of primary carboxamides are formamide, acetamide, propionic acid amide, butyric acid amide, urea, oxalic acid diamide and malonic acid diamide.

The acylation catalyst may be used in catalytic or up to stoichiometric amounts or in excess, based on the aromatic compound. The amount may be, for example, 0.01 to 500, preferably 0.1 to 150, most preferably 1 to 100 mol %, based on the aromatic compound.

Acylation catalysts are known per se, whereby in general organic nitriles and especially N-basic compounds with an imine group are primarily used.

The acylation catalysts are, for example, nitrogen bases with an imine group, which have a $pK_a$ value of at least 4 and up to 12. The $pK_a$ value is preferably 5 to 10.

The acylation catalysts are in particular organic N-basic compounds with an imine group, whereby heterocyclic and heteroaromatic compounds are preferred. Examples are 2H-pyrrole, imidazole, pyrazole, pyridine, pyrazine, pyrimidine, pyridazine, 3H-indole, 1H-indazole, purine, isoquinoline, quinoline, phthalazine, naphthydrine, quinoxaline, quinazoline, pteridine, acridine, phenanthroline, phenazine, imidazoline, triazine, 2-piccoline, lutidine, benzimidazole, methylimidazole, pyrazole, 4-dimethylaminopyridine, 4-pyrrolidinopyridine, 1,3,5-triazine and 4-methylaminopyridine.

The process according to the invention may be carried out without or in the presence of an inert solvent. Suitable solvents are, for example aliphatic, cycloaliphatic and aromatic hydrocarbons (pentane, hexane, petroleum ether, cyclohexane, methylcyclohexane, benzene, toluene, xylene), aliphatic halogen-hydrocarbons (methylene chloride, chloroform, di- and tetrachloroethane), nitriles (acetonitrile, propionitrile, benzonitrile), ethers (diethylether, dibutylether, tert.-butylmethylether, ethylene glycol dimethylether, ethylene glycol diethylether, diethylene glycol dimethylether, tetrahydrofuran, dioxane, diethylene glycol monomethyl- or monoethylether), ketones (acetone, methyl isobutyl ketone), carboxylates and lactones (ethyl and methyl acetate, valerolactone), N-substituted lactams (N-methylpyrrolidone), carboxamides (dimethylamide, dimethylformamide), acyclic ureas (dimethyl imidazolinum), and sulphoxides and sulphones (dimethyl sulphoxide, dimethyl sulphone, tetramethylene sulphoxide, tetramethylene sulphone).

One preferred embodiment of the process according to the invention consists in the simultaneous use of formamide as the amidation agent and solvent.

The process according to the invention may be carried out for example in such a way that the isolated Pd(0) catalyst is placed in an agitating autoclave, or a Pd compound or a heterogeneous Pd catalyst is placed in the autoclave optionally together with an excess of complexing ligands, and then the acylation catalyst is added. Afterwards, the aromatic compound containing a leaving group is added, and also optionally a solvent, and the autoclave is closed. Prior to the start of the reaction, the autoclave may be flushed with an inert gas, for example nitrogen. Then, carbon monoxide is applied, the reaction mixture is heated for a lengthy period of time and allowed to cool after the reaction, then isolated and the primary aromatic carboxamide obtained is purified by known methods, for example by extraction, crystallisation, distillation and chromatography. It may be advantageous to add water-binding agents to the reaction mixture, for example molecular sieves.

The aromatic carboxamides produced according to the invention are valuable intermediates in the preparation of pharmaceutical and pesticidal compositions, see for example EP-A-0 225 673, EP-A-0 279 633 and EP-A-0 753 508.

The following examples illustrate the invention more fully.

EXAMPLE 1

Preparation of 3-(trifluoromethyl)-benzoic Acid Amide 0.491 g of bis(triphenylphosphine)-palladium(II)chloride, 0.371 g of triphenylphosphine and 2.6 g of imidazole are placed in a 200 ml glass autoclave, and then 8.01 g of 3-(trifluoromethyl)bromobenzene, 25 ml of formamide and 810.3 mg of diethylene glycol dibutylether are added as an internal gas chromatography (GC) standard. The autoclave is closed, flushed with nitrogen three times and then 5 bars carbon monoxide are applied. The reaction mixture is heated to 120° C. and stirred for 14 hours. The mixture is then cooled and the content determined by GC (0.8 ml of reaction mixture mixed with 5 ml of water, then 2 ml of diethylether added, and GC determination effected with the organic phase). The yield of title compound is 82% by weight.

$^1$H-NMR: 5.6–6.4 (br, d NH$_2$), 7.61 (t, Ph—H), 7.80 (d, Ph—H), 8.01 (d, Ph—H), 8.11 (s, Ph—H).

EXAMPLE 2

Preparation of 3-(trifluoromethyl)-benzoic Acid Amide

The process is carried out analogously to example 1, but adding 4.2 g of 2,4-lutidine instead of imidazole. The yield of title compound is 75% by weight.

EXAMPLE 3

Preparation of 3-(trifluoromethyl)-benzoic Acid Amide

The process is carried out analogously to example 1, but adding 77 mg of Pd(OAc)$_2$ and 0.366 g of triphenylphosphine instead of bis(triphenylphosphine)-palladium(II) chloride, and adding 4.74 g of 4-dimethylaminopyridine instead of imidazole. The yield of title compound is 100% by weight. OAc signifies acetate.

EXAMPLE 4

Preparation of 3-(trifluoromethyl)-benzoic Acid Amide

The process is carried out analogously to example 3, but the catalyst is preformulated with 7.7 mg of Pd(OAc)$_2$ and 36.6 mg of triphenylphosphine. The yield of title compound is 95% by weight.

EXAMPLE 5

Preparation of 3-(trifluoromethyl)-benzoic Acid Amide

The process is carried out analogously to example 3, but adding 183 mg of PdCl$_2$ solution (20% Pd) and 0.169 g of 1-{(R)-1-[2-(S)-(diphenylphosphino)ferrocenyl]-ethyl)}-3,5-dimethyl-1H-pyrazole(PN ligand) instead of Pd(OAc)$_2$ and triphenylphosphine. The yield of title compound is 70% by weight.

EXAMPLE 6

Preparation of 3-(trifluoromethyl)-benzoic Acid Amide

The process is carried out analogously to example 3, but adding 0.757 g of 5% PdO/C instead of Pd(OAc)$_2$. The yield of title compound is 98% by weight.

EXAMPLE 7

Preparation of 3-(trifluoromethyl)-benzoic Acid Amide

The process is carried out analogously to example 3, but adding 0.431 g of 4-dimethylamino-pyridine and 7.11 g of tributylamine. The yield of title compound is 96% by weight.

EXAMPLE 8

Preparation of 3-(trifluoromethyl)-benzoic Acid Amide

The process is carried out analogously to example 3, but using instead of 25 ml of formamide, 1.712 g of formamide and 25 ml of cyclohexane. The yield of title compound is 100% by weight.

EXAMPLE 9

Preparation of 3-(trifluoromethyl)-benzoic Acid Amide

The process is carried out analogously to example 3, but using 0.366 g of $PdCl_2$ solution (20% Pd) instead of $Pd(OAc)_2$, and using 1.712 g of formamide and 25 ml of acetonitrile instead of 25 ml of formamide. The yield of title compound is 70% by weight.

EXAMPLE 10

Preparation of 3-(trifluoromethyl)-benzoic Acid Amide

The process is carried out analogously to example 3, but using 0.243 g of bis(triphenylphosphine)-palladium(II) chloride instead of $Pd(OAc)_2$, and using 7.8 g of formamide and 25 ml of dioxane instead of 25 ml of formamide. The yield of title compound is 92% by weight.

EXAMPLE 11

Preparation of 3-(trifluoromethyl)-benzoic Acid Amide

The process is carried out analogously to example 3, but using 0.243 g of bis(triphenyl-phosphine)-palladium (II) chloride instead of $Pd(OAc)_2$, and using 15.6 g of formamide and 25 ml of 1-methyl-pyrrolidinone instead of 25 ml of formamide. The yield of title compound is 87% by weight.

EXAMPLE 12

Preparation of 3-(trifluoromethyl)-benzoic Acid Amide

The process is carried out analogously to example 3, but using 0.243 g of bis(triphenylphosphine)-palladium(II) chloride instead of $Pd(OAc)_2$, and using 7.8 g of formamide and 25 ml of 2-butanone instead of 25 ml of formamide. The yield of title compound is 93% by weight.

EXAMPLE 13

Preparation of 3-(trifluoromethyl)-benzoic Acid Amide

The process is carried out analogously to example 3, but using 0.243 g of bis(triphenylphosphine)-palladium(II) chloride instead of $Pd(OAc)_2$, and using 7.8 g of formamide and 25 ml of n-butyl acetate instead of 25 ml of formamide. The yield of title compound is 99% by weight.

EXAMPLE 14

Preparation of 3-(trifluoromethyl)-benzoic Acid Amide

The process is carried out analogously to example 3, but using 0.243 g of bis(triphenylphosphine)-palladium(II) chloride instead of $Pd(OAc)_2$, and using 4.17 g of urea and 25 ml of N,N-dimethylacetamide instead of 25 ml of formamide. The yield of title compound is 54% by weight.

EXAMPLE 15

Preparation of 4-Acetylbenzamide 0.122 g of bis(triphenylphosphine)-palladium(II) chloride, 3.439 g of 4-bromoacetophenone, 3.12 g of formamide, 2.37 g of 4-dimethylamino-pyridine and 20 ml of 1-methyl-2-pyrrolidinone are placed in a 200 ml glass autoclave. The autoclave is closed, flushed with nitrogen three times and then 5 bars carbon monoxide are applied. The reaction mixture is heated to 120° C. and stirred for 18 hours. It is then cooled, and the solution is diluted with ethyl acetate and water, and extracted. The aqueous phase is extracted by shaking 3 times with ethyl acetate, and afterwards the organic phases are collected, dried over magnesium sulphate and concentrated. The oil obtained is chromatographed over silica gel. The yield of title compound is 35% (part of the product remains in the water phase).

$^{13}$C-NMR: 27.7 (Me), 128.7 (2 Ph—CH), 138.9 (Ph—C), 139.9 (2 Ph—CH), 139.5 (Ph—C), 168.0 ($CONH_2$), 198.5 (COMe).

EXAMPLE 16

Preparation of 4-cyanobenzamide 0.127 g of bis(tricyclohexylphosphine)-palladium, 2.377 g of 4-chlorobenzonitrile, 3.12 g of formamide, 2.82 g of 4-pyrrolidinopyridine and 20 ml of 1-methyl-2-pyrrolidinone are placed in a 200 ml glass autoclave. The autoclave is closed, flushed with nitrogen three times and then 5 bars carbon monoxide are applied. The reaction mixture is heated to 120° C. and stirred for 18 hours. It is then cooled, the white precipitate is filtered and mixed with ethyl acetate and water, and extracted. The aqueous phase is extracted by shaking 3 times with ethyl acetate, and afterwards the organic phases are collected, dried over magnesium sulphate and concentrated. The oil obtained is chromatographed over silica gel. The yield of title compound is 40% (part of the product remains in the water phase).

$^{13}$C-NMR: 115.1 (Ph—C), 118.6 (CN), 128.8 (2 Ph—CH), 132.8 (2 Ph—CH), 138.7 (Ph—C), 168.6 ($CONH_2$).

EXAMPLE 17

Preparation of Pyridine-2-carboxamide 0.255 g of bis(tricyclohexylphosphine)-palladium(II) dichloride, 5.458 g of 2-chloropyridine, 3.12 g of formamide, 4.64 g of 4-dimethylamino-pyridine and 25 ml of acetonitrile are placed in a 200 ml glass autoclave. The autoclave is closed, flushed with nitrogen three times and then 5 bars carbon monoxide are applied. The reaction mixture is heated to 120° C. and stirred for 18 hours. It is then cooled, and the suspension is mixed with ethyl acetate and water, and extracted. The aqueous phase is extracted by shaking 3 times with ethyl acetate, and afterwards the organic phases are collected, dried over magnesium sulphate and concentrated. The oil obtained is chromatographed over silica gel. The yield of title compound is 36% (part of the product remains in the water phase).

$^{13}$C-NMR: 122.8 (Ph—CH), 126.8 (Ph—CH), 138.1 (Ph—CH), 149.0 (Ph—CH), 150.0 (Ph—C), 167.5 ($CONH_2$).

EXAMPLE 18

Preparation of Cinnamic Acid Amide 0.249 g of bis(triphenylphosphine)-palladium(II) chloride, 6.51 g of (2-bromovinyl)benzene, 3.03 g of formamide, 4.78 g of 4-dimethylamino-pyridine and 25 ml of dimethylacetamide are placed in a 200 ml glass autoclave. The autoclave is closed, flushed with nitrogen three times and then 5 bars carbon monoxide are applied. The reaction mixture is heated to 120° C. and stirred for 18 hours. It is then cooled, and the solution is diluted with diethylether and water, and extracted. The aqueous phase is extracted by shaking 3 times with diethylether, and afterwards the organic phases are collected, dried over magnesium sulphate and concentrated. The oil obtained is chromatographed over silica gel. The yield of title compound is 26% (part of the product remains in the water phase).

$^{13}$C-NMR: 117.9 (Ph—CH), 128.2 (2 Ph—CH), 129.3 (2 Ph—CH), 129.9 (C=CH), 135.8 (Ph—C), 142.7 (C=CH), 167.1 (CONH$_2$).

EXAMPLE 19

Preparation of 4-dimethylamine-benzamide 0.255 g of bis(tricyclohexylphosphine)-palladium(II) dichloride, 6.91 g of 4-bromo-N,N-dimethylaniline, 3.12 g of formamide, 4.64 g of 4-dimethylamino-pyridine and 25 ml of dimethyl acetamide are placed in a 200 ml glass autoclave. The autoclave is closed, flushed with nitrogen three times and then 5 bars carbon monoxide are applied. The reaction mixture is heated to 120° C. and stirred for 18 hours. It is then cooled, and the suspension is mixed with ethyl acetate and water, and extracted. The aqueous phase is extracted by shaking 3 times with ethyl acetate, and afterwards the organic phases are collected, dried over magnesium sulphate and concentrated. The oil obtained is chromatographed over silica gel. The yield of title compound is 29% (part of the product remains in the water phase).
$^{13}$C-NMR: 40.6 (NMe$_2$), 11.4 (2 Ph—CH), 123.5 (Ph—C), 129.9 (2 Ph—CH), 151.7 (Ph—C), 172.6 (CONH$_2$).

EXAMPLE 20

Preparation of 4-tert.-butyl-benzamide 0.255 g of bis(triphenylphosphine)-palladium(II) chloride, 7.36 g of 1-bromo-4-tert-butylbenzene, 3.12 g of formamide, 4.64 g of 4-dimethylamino-pyridine and 25 ml of dimethyl acetamide are placed in a 200 ml glass autoclave. The autoclave is closed, flushed with nitrogen three times and then 5 bars carbon monoxide are applied. The reaction mixture is heated to 120° C. and stirred for 18 hours. It is then cooled, and the solution is diluted with diethylether and water, and extracted. The aqueous phase is extracted by shaking 3 times with diethylether, and afterwards the organic phases are collected, dried over magnesium sulphate and concentrated. The oil obtained is chromatographed over silica gel. The yield of title compound is 33% (part of the product remains in the water phase).
$^1$H-NMR: 1.35 (s, CMe$_3$), 6.21 (br, NH$_2$), 7.45 (d, Ph—H), 7.77 (d, Ph—H); $^{13}$C-NMR: 31.5 (CMe$_3$), 35.4 (C—Me), 125.9 (2 Ph—CH), 127.6 (2 Ph—CH), 130.9 (Ph—C), 155.1 (Ph—C), 169.9 (CONH$_2$).

EXAMPLE 21

Preparation of Pyridine-2-carboxamide 0.255 g of bis(tricyclohexylphosphine)-palladium(II) dichloride, 3.923 g of 2-chloropyridine, 3.12 g of formamide, 4.64 g of 4-dimethylamino-pyridine and 25 ml of dimethyl acetamide are placed in a 200 ml glass autoclave. The autoclave is closed, flushed with nitrogen three times and then 5 bars carbon monoxide are applied. The reaction mixture is heated to 120° C. and stirred for 18 hours. It is then cooled, and the suspension is mixed with ethyl acetate and water, and extracted. The aqueous phase is extracted by shaking 3 times with ethyl acetate, and afterwards the organic phases are collected, dried over magnesium sulphate and concentrated, The oil obtained is chromatographed over silica gel. The yield of title compound is 18% (part of the product remains in the water phase).

What we claim is:

1. Process for the preparation of primary aromatic carboxamides by the carbonylation of an aromatic compound, which contains at least one leaving group, with carbon monoxide, in the presence of a homogeneous or heterogeneous Pd catalyst and at least stoichiometric amounts of an amidation agent at elevated temperatures, wherein a primary carboxamide or a primary urethane is used as the amidation agent, and the reaction is carried out in the presence of an acylation catalyst.

2. Process according to claim 1, wherein the amidation agent is a carboxamide of mono- or polycarboxylic acids, or urea.

3. Process according to claim 1, wherein the primary carboxamides correspond to formula I,

$$R_1[C(O)\text{—}NH_2]_x \qquad (I),$$

wherein x is 1, and $R_1$ signifies H, NH$_2$, OR$_2$ or linear or branched alkyl with 1 to 6 carbon atoms, or wherein x is 2 and $R_1$ signifies a direct bond or linear or branched alkylene with 1 to 6 carbon atoms, and $R_2$ is linear or branched alkyl with 1 to 6 carbon atoms.

4. Process according to claim 3, wherein (a) x is equal to 1 and $R_1$ is H, NH$_2$, methyl, ethyl, n- or iso-propyl, n-, iso- or tert-butyl, and (b) x is equal to 2 and $R_1$ signifies methylene, ethylidene, 2,2-propylidene, ethylene, methylethylene, 1,3-propylene or 1,2-, 1,3- or 1,4-butylidene.

5. Process according to claim 3, wherein formamide, acetamide, propionic acid amide, butyric acid amide, urea, oxalic acid diamide or malonic acid diamide is used as the amidation agent.

6. Process according to claim 3, wherein formamide or urea is used as the amidation agent.

7. Process according to claim 6, wherein formamide is used simultaneously as the amidation agent and as the solvent.

8. Process according to claim 1, wherein the acylation catalyst is used in an amount of 0.1 to 500 mol % based on the aromatic compound.

9. Process according to claim 1, wherein nitrogen bases with an imine group, which have a pK$_a$ value of 4 to 12, are used as acylation catalysts.

10. Process according to claim 8, wherein the acylation catalyst is selected from the group 2H-pyrrole, imidazole, pyrazole, pyridine, pyrazine, pyrimidine, pyridazine, 3H-indole, 1H-indazole, purine, isoquinoline, quinoline, phthalazine, naphthydrine, quinoxaline, quinazoline, pteridine, acridine, phenanthroline, phenazine, imidazoline, triazine, 2-piccoline, lutidine, benzimidazole, methylimidazole, pyrazole, 4-dimethylaminopyridine, 4-pyrrolidinopyridine, 1,3,5-triazine and 4-methylaminopyridine.

11. Process according to claim 1, wherein the Pd catalyst is used in an amount of 0.001 to 10 mol % based on the aromatic compound.

12. Process according to claim 1, wherein the Pd catalyst is selected from Pd(0) complexes with ligands from the group of mono- or bidentate, tertiary or ditertiary amines, phosphines and arsines.

13. Process according to claim 12, wherein the ligand is selected from the group of mono- or bidentate, tertiary or ditertiary phosphines.

14. Process according to claim 12, wherein the Pd catalyst is formed in situ from Pd(II) or Pd(0) compounds, from colloidal Pd(0), from Pd(0) applied to carrier materials, or from Pd(II) compounds applied to carrier materials, by complexing with ligands.

15. Process according to claim 1, wherein the aromatic compounds, which contain a leaving group, are hydrocarbon aromatics, hetero-aromatics or aryl- or heteroaryl-vinyls with a leaving group on a vinyl carbon atom.

16. Process according to claim 1, wherein the leaving group is a halide.

17. Process according to claim 16, wherein the leaving group is a chloride or bromide.

18. Process according to claim 1, which is carried out at high pressure.

19. Process according to claim 18, which is carried out at a pressure of 1 to 20 bar.

20. Process according to claim 1, which is carried out at a temperature of 30 to 250° C.

21. Process according to claim 3, wherein the alkyl has 1 to 4 carbon atoms and the alkylene has 1 to 4 carbon atoms.

* * * * *